US00PP12954P2

(12) United States Plant Patent
Dekker

(10) Patent No.: US PP12,954 P2
(45) Date of Patent: Sep. 17, 2002

(54) CHRYSANTHEMUM PLANT NAMED 'CREAM EUROBELLE'

(75) Inventor: Niek Dekker, Hensbroek (NL)

(73) Assignee: Dekker Breeding B.V., Hensbroek (NL)

( * ) Notice: Subject to any disclaimer, the term of this patent is extended or adjusted under 35 U.S.C. 154(b) by 18 days.

(21) Appl. No.: 09/653,171

(22) Filed: Aug. 31, 2000

(51) Int. Cl.[7] ..... A01H 5/00
(52) U.S. Cl. ..... Plt./289
(58) Field of Search ..... Plt./289

*Primary Examiner*—Bruce R. Campell
*Assistant Examiner*—Anne Marie Grünberg

(57) ABSTRACT

A distinct cultivar of Chrysanthemum plant named 'Cream Eurobelle', characterized by its light yellow decorative inflorescences with green centers; dark green foliage; early response time; and good post-production longevity.

2 Drawing Sheets

BACKGROUND OF THE INVENTION

The present invention relates to a new and distinct cultivar of Chrysanthemum plant, botanically known as *Dendranthema grandiflora* and referred to by the cultivar name Cream Eurobelle.

The new Chrysanthemum was discovered by the Inventor in a controlled environment in Hensbroek, The Netherlands in 1999, as a naturally-occurring whole plant mutation of the *Dendranthema grandiflora* cultivar Eurobelle, U.S. Plant patent application Ser. No. 09/653,172. The new Chrysanthemum was observed as a single plant in a group of flowering plants of the parent cultivar. The selection of this plant was based on its unique ray floret color.

Asexual reproduction of the new Chrysanthemum by terminal cuttings harvested in Hensbroek, The Netherlands, has shown that the unique features of this new Chrysanthemum are stable and reproduced true to type in successive generations.

BRIEF SUMMARY OF THE INVENTION

The cultivar Cream Eurobelle has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Cream Eurobelle'. These characteristics in combination distinguish 'Cream Eurobelle' as a new and distinct cultivar:

1. Light yellow decorative inflorescences with green centers.
2. Dark green foliage.
3. Early response time.
4. Good post-production longevity.

Plants of the new Chrysanthemum differ from plants of the parent cultivar, Eurobelle, primarily in ray floret color.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new Chrysanthemum.

The photograph on the first sheet comprises a side perspective view of a typical flowering stem of 'Cream Eurobelle'.

The photograph at the top of the second sheet comprises a close-up view of typical inflorescences of 'Cream Eurobelle'.

The photograph at the bottom of the second sheet comprises a close-up view of the upper and lower surfaces of typical leaves of 'Cream Eurobelle'.

DETAILED BOTANICAL DESCRIPTION

In the following description, color references are made to The Royal Horticultural Society Colour Chart except where general terms of ordinary dictionary significance are used. The following observations and measurements describe plants grown in Hensbroek, The Netherlands, under commercial practice in a glass-covered greenhouse. Rooted cuttings were planted mid-February, 2000, in soil beds and given about 21 long days/short nights before starting the photoinductive short day/long night treatment. Average day and night temperatures were about 20 and 18° C., respectively, and light level was about 30,000 lux. Measurements and numerical values represent averages for typical flowering stems.

Botanical classification: *Dendranthema grandiflora* cultivar Cream Eurobelle.

Commercial classification: Decorative-type cut Chrysanthemum.

Patentage: Naturally-occurring whole plant mutation of *Dendranthema grandiflora* cultivar Eurobelle, U.S. Plant patent application Ser. No. 09/653,172.

Propagation:

*Type.*—Terminal tip cuttings.

*Time to initiate and develop roots, summer.*—About 14 days at temperatures about 20° C.

*Time to initiate and develop roots, winter.*—About 16 days at temperatures about 20° C.

*Rooting habit.*—Fine, fibrous and well-branched.

Plant description:

*Appearance.*—Herbaceous decorative-type cut Chrysanthemum, typically grown as a spray-type.

*Growth rate.*—Moderate growth rate; vigorous.

*Stem description.*—Length: About 70 to 80 cm. Strength: Strong. Aspect: Upright. Color: 146B.

*Foliage description.*—Arrangement: Alternate. Quantity of leaves per main stem: About 18 to 23. Length: About 11 cm. Width: About 7 cm. Apex: Acute. Base: Acuminate. Margin: Palmately lobed. Texture: Rough; both surfaces pubescent. Petiole length: About 2.5 cm. Color: Young and mature foliage upper surface: 147A. Young and mature foliage lower surface: 147B. Venation upper and lower surfaces: 147C. Petiole: 147C.

Inflorescence description:

*Appearance.*—Decorative-type inflorescence form. Inflorescences borne on terminals, arising from leaf axils. Disc and ray florets arranged acropetally on the receptacle.

*Flowering response.*—Under natural conditions, plant flower in the autumn/winter in the Northern Hemisphere. At other times of the year, inflorescence initiation and development can be induced under short day/long night conditions (at least 13.5 hours of darkness). Plants exposed to three weeks of long day/short night conditions after planting followed by photoinductive short day/long night conditions flower about 53 days later.

*Post-production longevity.*—Cut flowering stems of the new Chrysanthemum last about two to three weeks after harvesting.

*Quantity of inflorescences per flowering stem.*—About 13 to 18.

*Inflorescence size.*—Diameter: About 7 cm. Depth (height): About 2.5 cm. Diameter of disc: About 8 mm.

*Inflorescence buds.*—Length: About 9 mm. Diameter: About 11.5 mm. Shape: Spherical. Color: 138A.

*Ray florets.*—Length, largest florets: About 3.5 cm. Width, largest florets: About 1.3 cm. Shape: Elongated oblong; concave. Apex: Praemorse. Base: Fused, tubular. Texture: Smooth, glabrous. Number of ray florets per inflorescence: About 180. Color: When opening: Apex, 142B; base, 155B to 155C. Mature, upper and lower surfaces: Apex, 3C; base, 155B. Color fading to 155A with subsequent development.

*Disc florets.*—Shape: Tubular. Length: About 5 mm. Width: About 1.5 mm. Number of disc florets per inflorescence: About 10. Color: Immature: 155A. Mature: Apex, 145A; mid-section, 155B; base, 155A.

*Peduncles.*—Length, terminal peduncle: About 8 cm. Length, fourth peduncle: About 13 cm. Diameter: About 2.5 mm. Angle: About 60° to main stem. Texture: Pubescent. Color: 146B.

*Reproductive organs.*—Androecium: Present on disc florets only. Anther color: 151B. Pollen amount: Scarce. Pollen: 23A. Gynoecium: Present on both ray and disc florets. Stigma length: About 1 mm. Stigma diameter: About 0.3 mm. Stigma color: Apex, 151B; base, 144C to 144D.

*Seed.*—Seed production has not been observed.

Disease resistance: Resistance to known Chrysanthemum diseases has not been observed on plants of the new Chrysanthemum grown under commercial conditions.

It is claimed:

1. A new and distinct cultivar of Chrysanthemum plant named 'Cream Eurobelle', as illustrated and described.

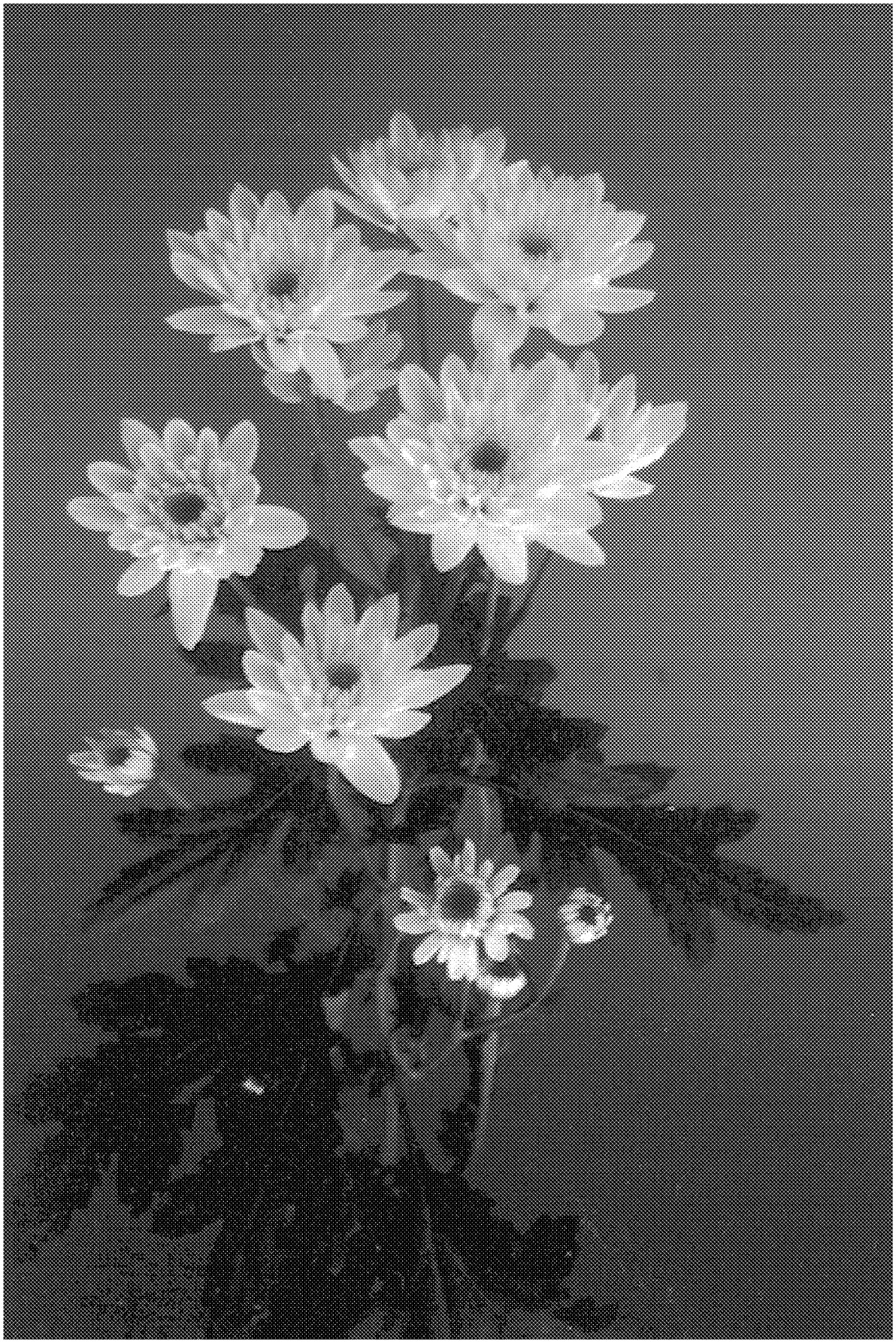

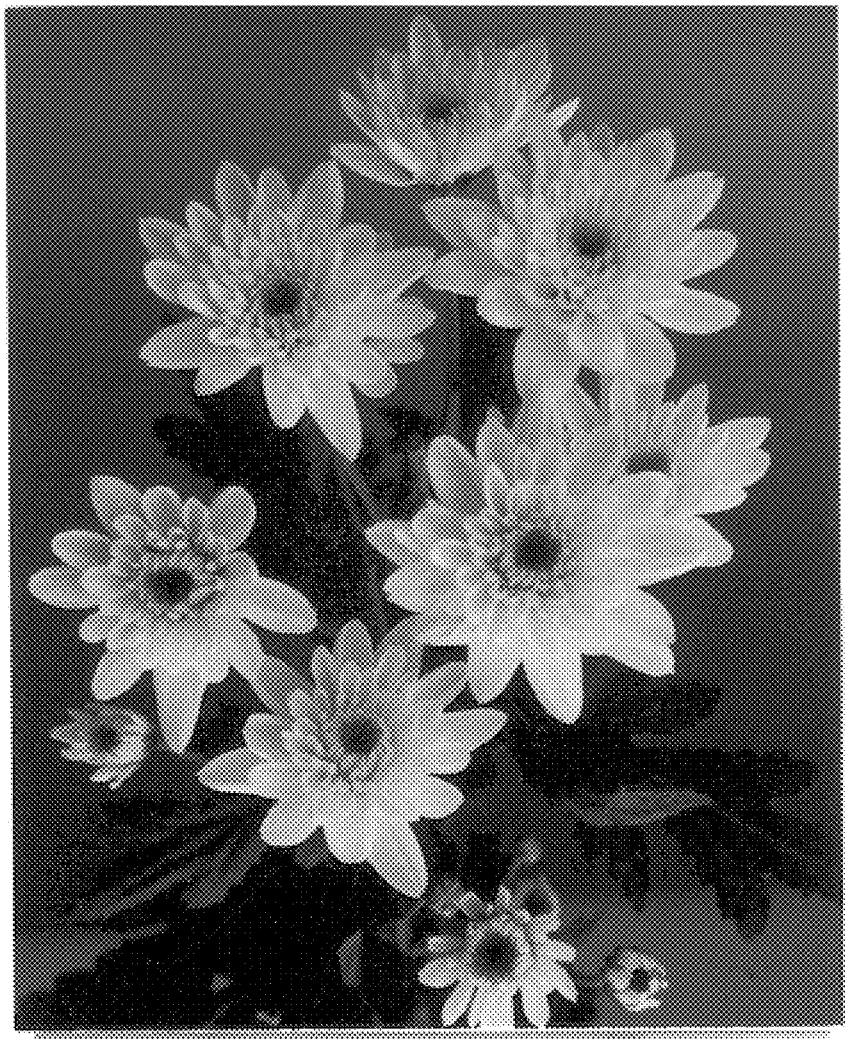
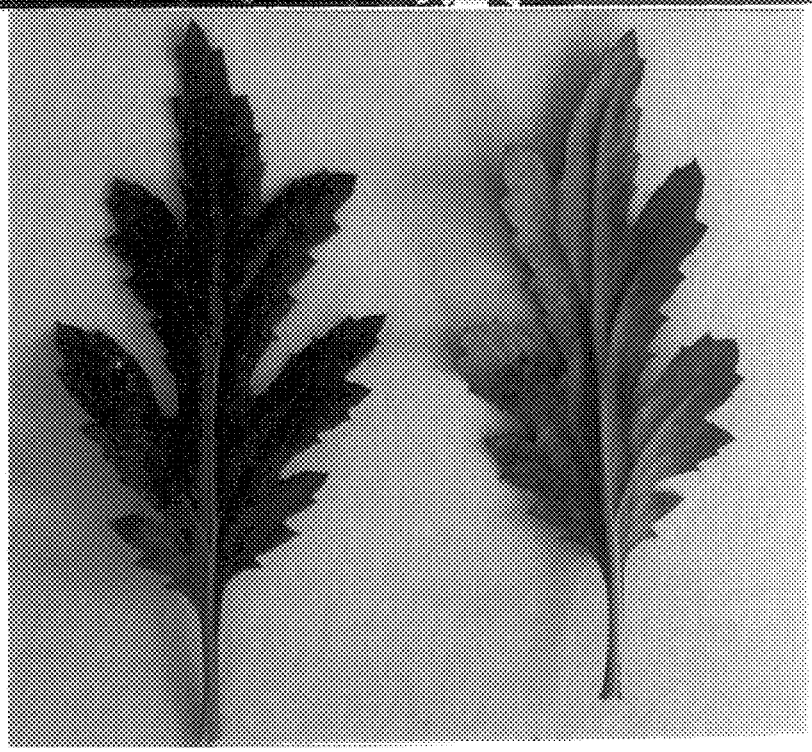

* * * * *